US008680321B2

(12) United States Patent
Johnston et al.

(10) Patent No.: US 8,680,321 B2
(45) Date of Patent: Mar. 25, 2014

(54) PROCESSES FOR MAKING ETHANOL FROM ACETIC ACID USING BIMETALLIC CATALYSTS

(75) Inventors: Victor J. Johnston, Houston, TX (US); Laiyuan Chen, Houston, TX (US); Barbara F. Kimmich, Bernardsville, NJ (US); Josefina T. Chapman, Houston, TX (US); James H. Zink, League City, TX (US); Heiko Weiner, Pasadena, TX (US); John L. Potts, Angleton, TX (US); Radmila Jevtic, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 907 days.

(21) Appl. No.: 12/699,003

(22) Filed: Feb. 2, 2010

(65) Prior Publication Data

US 2011/0098501 A1 Apr. 28, 2011

Related U.S. Application Data

(63) Continuation-in-part of application No. 12/588,727, filed on Oct. 26, 2009, now Pat. No. 8,309,772.

(51) Int. Cl.
*C07C 67/08* (2006.01)

(52) U.S. Cl.
USPC .......................................... 560/129

(58) Field of Classification Search
USPC .......................................... 560/129
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Adam |
| 3,702,886 A | 11/1972 | Argauer et al. |
| 3,729,429 A | 4/1973 | Robson |
| 3,864,284 A | 2/1975 | Clippinger et al. |
| 3,990,952 A | 11/1976 | Katzen et al. |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Gruffaz et al. |
| 4,317,918 A | 3/1982 | Takano et al. |
| 4,328,373 A | 5/1982 | Strojny |
| 4,337,351 A | 6/1982 | Larkins, Jr. |
| 4,374,265 A | 2/1983 | Larkins, Jr. |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,443,639 A | 4/1984 | Pesa et al. |
| 4,465,854 A | 8/1984 | Pond et al. |
| 4,471,136 A | 9/1984 | Larkins et al. |
| 4,480,115 A | 10/1984 | McGinnis |
| 4,517,391 A | 5/1985 | Schuster et al. |
| 4,521,630 A | 6/1985 | Wattimena et al. |
| 4,550,185 A * | 10/1985 | Mabry et al. .................. 549/508 |
| 4,581,473 A | 4/1986 | Polichnowski |
| 4,613,700 A | 9/1986 | Maki et al. |
| 4,620,050 A | 10/1986 | Cognion et al. |
| 4,678,543 A | 7/1987 | Houben et al. |
| 4,692,218 A | 9/1987 | Houben et al. |
| 4,696,596 A | 9/1987 | Russell et al. |
| 4,777,303 A | 10/1988 | Kitson et al. |
| 4,804,791 A | 2/1989 | Kitson et al. |
| 4,826,795 A | 5/1989 | Kitson et al. |
| 4,843,170 A | 6/1989 | Isshiki et al. |
| 4,886,905 A | 12/1989 | Larkins, Jr. |
| 4,978,778 A | 12/1990 | Isshiki et al. |
| 4,985,572 A | 1/1991 | Kitson et al. |
| 4,990,655 A | 2/1991 | Kitson et al. |
| 5,008,235 A | 4/1991 | Wegman et al. |
| 5,061,671 A | 10/1991 | Kitson et al. |
| 5,124,004 A | 6/1992 | Grethlein et al. |
| 5,137,861 A | 8/1992 | Shih et al. |
| 5,149,680 A * | 9/1992 | Kitson et al. .................. 502/185 |
| 5,155,084 A | 10/1992 | Horn et al. |
| 5,185,308 A | 2/1993 | Bartley et al. |
| 5,241,106 A | 8/1993 | Inoue et al. |
| 5,243,095 A | 9/1993 | Roberts et al. |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Carole, TM, Pellegrino, J, and Paster, MD, "Opportunities in the Industrial Biobased Products Industry" App. Biochem & Biotech. 2004,115, 871-885.*

(Continued)

*Primary Examiner* — Johann R Richter
*Assistant Examiner* — Kofi Adzamli

(57) ABSTRACT

A process for selective formation of ethanol and/or ethyl acetate from acetic acid by hydrogenating acetic acid in the presence of a Pt/Sn catalyst or a Re/Pd catalyst. The catalyst may further comprise a support modifier to improve selectivity for the desired product.

14 Claims, 2 Drawing Sheets

(56) References Cited

U.S. PATENT DOCUMENTS

| | | |
|---|---|---|
| 5,306,845 A | 4/1994 | Yokohama et al. |
| 5,350,504 A | 9/1994 | Dessau et al. |
| 5,426,246 A | 6/1995 | Nagahara et al. |
| 5,475,144 A | 12/1995 | Watson et al. |
| 5,476,827 A | 12/1995 | Ferrero et al. |
| RE35,377 E | 11/1996 | Steinberg et al. |
| 5,585,523 A | 12/1996 | Weiguny et al. |
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Grady et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 6,008,384 A | 12/1999 | Bockrath et al. |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,232,352 B1 | 5/2001 | Vidalin et al. |
| 6,232,504 B1 | 5/2001 | Barteau et al. |
| 6,294,703 B1 | 9/2001 | Hara et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B1 | 8/2006 | Huber et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,518,014 B2 | 4/2009 | Kimmich et al. |
| 7,538,060 B2 | 5/2009 | Bernicki et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,820,852 B2 | 10/2010 | Johnston et al. |
| 7,863,489 B2 | 1/2011 | Johnston et al. |
| 7,884,253 B2 | 2/2011 | Stites et al. |
| 7,994,368 B2 | 8/2011 | Johnston et al. |
| 8,071,821 B2 | 12/2011 | Johnston et al. |
| 8,309,772 B2 | 11/2012 | Weiner et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2004/0232049 A1 | 11/2004 | Dath et al. |
| 2006/0019360 A1 | 1/2006 | Verser et al. |
| 2006/0102520 A1 | 5/2006 | Lapinski et al. |
| 2006/0106246 A1 | 5/2006 | Warner et al. |
| 2006/0127999 A1 | 6/2006 | Verser et al. |
| 2007/0270511 A1 | 11/2007 | Melnichuk et al. |
| 2008/0207953 A1 | 8/2008 | Houssin et al. |
| 2008/0257784 A1 | 10/2008 | Dath et al. |
| 2008/0319236 A1 | 12/2008 | McNeff et al. |
| 2009/0005588 A1 | 1/2009 | Hassan et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0221725 A1 | 9/2009 | Chornet et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0113843 A1 | 5/2010 | Lee et al. |
| 2010/0121114 A1 | 5/2010 | Weiner et al. |
| 2010/0168493 A1 | 7/2010 | Le Peltier et al. |
| 2010/0196789 A1 | 8/2010 | Fisher et al. |
| 2010/0249479 A1 | 9/2010 | Berg-Slot et al. |
| 2011/0065572 A1 | 3/2011 | Olken et al. |
| 2011/0282109 A1 | 11/2011 | Johnston et al. |
| 2012/0253085 A1 | 10/2012 | Johnston et al. |

FOREIGN PATENT DOCUMENTS

| | | |
|---|---|---|
| CN | 102229520 | 11/2011 |
| EP | 0104197 | 4/1984 |
| EP | 0137749 A2 | 4/1984 |
| EP | 0167300 A1 | 1/1986 |
| EP | 0175558 | 3/1986 |
| EP | 0192587 | 8/1986 |
| EP | 0198682 B1 | 10/1986 |
| EP | 0285786 B1 | 5/1988 |
| EP | 0285420 | 10/1988 |
| EP | 0330853 | 9/1989 |
| EP | 0400904 | 5/1990 |
| EP | 0372847 A2 | 6/1990 |
| EP | 0408528 | 7/1990 |
| EP | 0407038 | 1/1991 |
| EP | 0285420 B1 | 10/1991 |
| EP | 0990638 | 4/2000 |
| EP | 1262234 | 12/2002 |
| EP | 1277826 | 1/2003 |
| EP | 2060553 A1 | 5/2009 |
| EP | 2060555 A1 | 5/2009 |
| EP | 2186787 | 5/2010 |
| GB | 1168785 | 10/1969 |
| GB | 1559540 | 1/1980 |
| GB | 2136704 | 9/1987 |
| JP | 6-116182 | 4/1994 |
| JP | 10-306047 A | 11/1998 |
| JP | 11-147845 | 6/1999 |
| JP | 2001-046874 A | 2/2001 |
| JP | 2001-157841 A | 6/2001 |
| WO | WO 83/03409 A1 | 10/1983 |
| WO | WO 03/040037 A1 | 5/2003 |
| WO | WO 2005/102513 | 11/2005 |
| WO | WO 2009/009322 A1 | 1/2009 |
| WO | WO 2009/009323 A1 | 1/2009 |
| WO | WO 2009/063176 A1 | 5/2009 |
| WO | WO 2009/086839 | 7/2009 |
| WO | WO 2009/105860 A1 | 9/2009 |
| WO | WO 2010/014145 A2 | 2/2010 |
| WO | WO 2010/014151 A1 | 2/2010 |
| WO | WO 2010/014153 A2 | 2/2010 |
| WO | WO 2010/055285 A1 | 5/2010 |
| WO | WO 2010/056299 | 5/2010 |
| WO | WO 2011/053365 | 5/2011 |

OTHER PUBLICATIONS

International Preliminary Report on Patentability for PCT/US2010/054136 mailed May 18, 2012.

(56) References Cited

OTHER PUBLICATIONS

U.S. Office Action mailed Oct. 15, 2012 in co-pending U.S. Appl. No. 12/850,414.
U.S. Office Action mailed Oct. 24, 2012 in co-pending U.S. Appl. No. 13/179,955.
U.S. Office Action mailed Nov. 29, 2012 in co-pending U.S. Appl. No. 12/699,024.
U.S. Office Action mailed Dec. 12, 2012 in co-pending U.S. Appl. No. 12/698,947.
Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.
Santori et al, (2000). Hydrogenation of carbonylic compounds on Pt/SiO2 catalysts modified with SnBu4, Studies in Surface Science and Catalysis, 130, 2063-2068.
Acala, et al. (2005). Experimental and DFT studies of the conversion of ethanol and acetic acid on PtSn-based catalysts, Journal of Physical Chemistry, 109(6), 2074-2085.
International Search Report and Written Opinion for PCT/US2010/022954 mailed Jun. 15, 2010.
International Written Opinion for PCT/US2010/022954 mailed Jan. 24, 2012.
International Preliminary Report on Patentability for PCT/US2010/022954 mailed Feb. 14, 2012.
Jingfa D., et al., "Acidic properties of ZSM-5 zeolite and conversion of ethanol to diethyl ether", Applied Catalysis, Amsterdam, NL, vol. 41, Jan. 1, 1988, pp. 13-22.
Nefedov and I V Mishin B K, "Synthesis of diethyl ether in presence of zeolite catalysts", Russian Chem. Bulletin, Springer New York LLC, US; RU, vol. 28, Jan. 1, 1979, pp. 183-186.
International Search Report and Written Opinion for PCT/US2010/054132 mailed Feb. 28, 2011.
International Written Opinion for PCT/US2010/054132 mailed Nov. 29, 2011.
International Preliminary Report on Patentability for PCT/US2010/054132 mailed Feb. 1, 2012.
International Search Report and Written Opinion for PCT/US2010/054134 mailed Feb. 28, 2011.
Rachmady, Acetic Acid Reduction by $H_2$ on Bimetallic Pt—Fe Catalysts, Journal of Catalysis 209, 87-98 (Apr. 1, 2002), Elsevier Science (USA).
Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.
Ordóñez et al., The role of metal and support sites on the hydrogenation of acetic acid on Ru-based catalysts, $21^{st}$ NAM San Francisco, CA, Jun. 10, 2009.
Pestman et al., The formation of ketones and aldehydes from carboxylic acids, structure-activity relationship for two competitive reactions, Journal of Molecular Catalysis A: Chemical 103 Jun. 14, 1995, 175-180.
Gursahani et al., Reaction kinetics measurements and analysis of reaction pathways for conversions of acetic acid, ethanol, and ethyl acetate over silica-supported Pt, Applied Catalysis A: General 222 (2001) 369-392.
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
ZeaChem, Inc., Technology Overview, Lakewood, Colorado www.zeachem.com, 2008.
Brunauer Emmett and Teller, J. Am. Chem. Soc. 60, 309 (1938).
Proc. Roy Soc. A314, pp. 473-498 (1970).
International Search Report and Written Opinion for PCT/US2009/004197 mailed Mar. 24, 2010 (14 pages).
International Search Report and Written Opinion for PCT/US2009/004195 mailed Mar. 26, 2010 (12 pages).
Pestman et al., Reactions of Carboxylic Acids on Oxides, Journal of Catalysis 168:255-264 (1997).
Pestman et al., Identification of the Active Sites in the Selective Hydrogenation of Acetic Acid to Acetaldehyde on Iron Oxide Catalysts, Journal of Catalysis 174:142-152 (1998).
Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.
Liberkova, and Tourounde, "Performance of Pt/SnO2 catalyst in the gas phase hydrogenation of crotonaldehyde," J. Mol. Catal. A: Chemical (2002), 180, pg. 221-230.
Rodrigues and Bueno, "Co/SiO2 catalysts for selective hydrogenation of crotonaldehyde: III. Promoting effect of zinc," Applied Catalysis A: General (2004), 257, p. 210-211.
Ammari, et al. "An emergent catalytic material: Pt/ZnO catalyst for selective hydrogenation of crotonaldehyde," J. Catal. (2004), 221, p. 32-42.
Ammari, et al. "Selective hydrogenation of crotonaldehyde on Pt/ZnCl2/SiO2 catalysts," J. Catal. (2005), 235, p. 1-9.
Consonni, et al. "High Performances of Pt/ZnO Catalysts in Selective Hydrogenation of Crotonaldehyde," J. Catal. (1999), 188, p. 165-175.
Nitta, et al. "Selective hydrogenation of $\alpha\beta$-unsaturated aldehydes on cobalt—silica catalysts obtained from cobalt chrysotile," Applied Catal. (1989), 56, p. 9-22.
International Search Report for PCT/US2010/022954 dated Sep. 7, 2011 (6 pages).
English Abstract for EP0330853, (Sep. 6, 1989).
English Abstract for CN1230458, (Oct. 6, 1999).
English Abstract for JP6-116182, (May 11, 2006).
English Abstract for JP11-147845, (Aug. 4, 2011).
Subramani et al., "A Review of Recent Literature to Search for an Efficient Catalytic Process for the Conversion of Syngas to Ethanol," Energy & Fuels, 2008, vol. 22, pp. 814-839.
Spivey et al., "Heterogeneous catalytic synthesis of ethanol from biomass-dervied syngas," Chemical Society Review, 2007, vol. 36, pp. 1514-1528.
T. Yokoyama et al., "Fine chemicals through heterogeneous catalysis. Carboxylic acids and derivitatives." 2001, pp. 370-379.

* cited by examiner

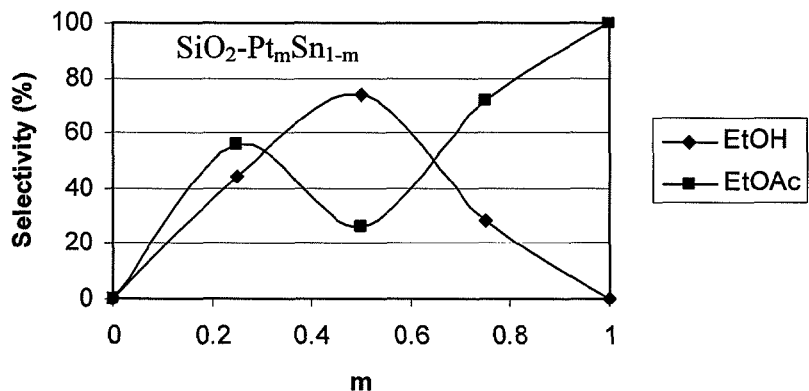
FIG. 1A - Selectivity Pt/Sn Catalyst
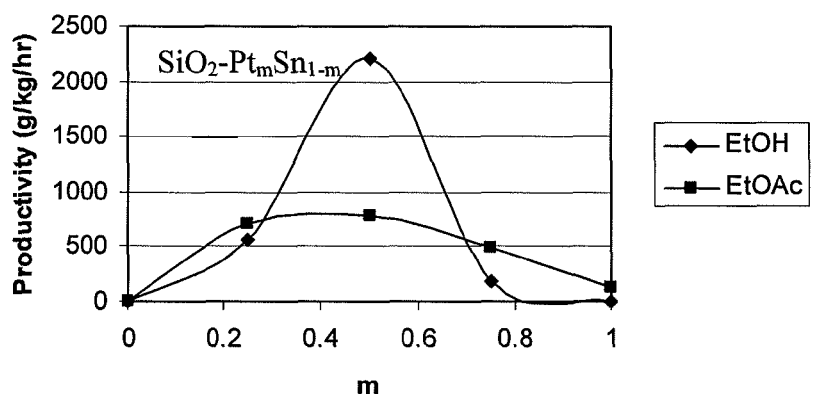
FIG. 1B - Productivity of Pt/Sn Catalyst
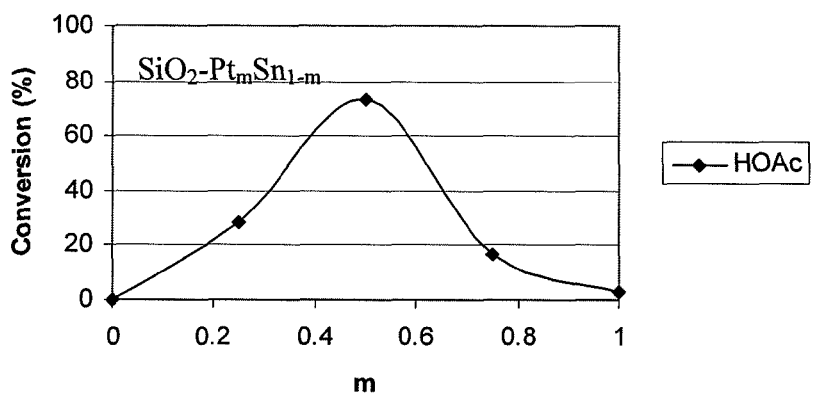
FIG. 1C - Conversion of HOAc

FIG. 2A - Selectivity of Re/Pd
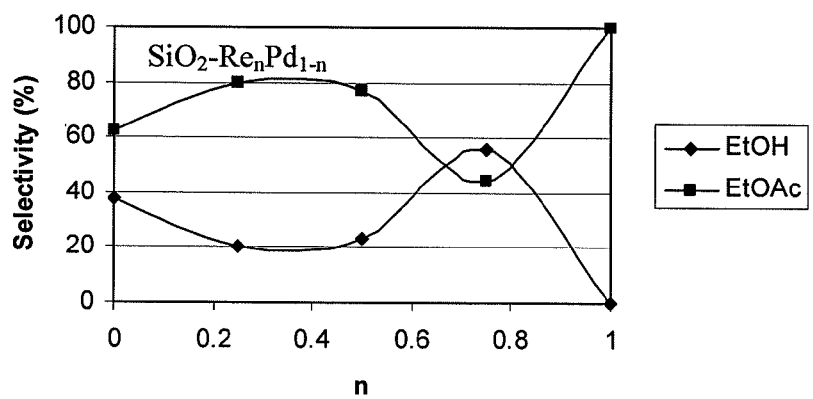
FIG. 2B - Productivity of Re/Pd
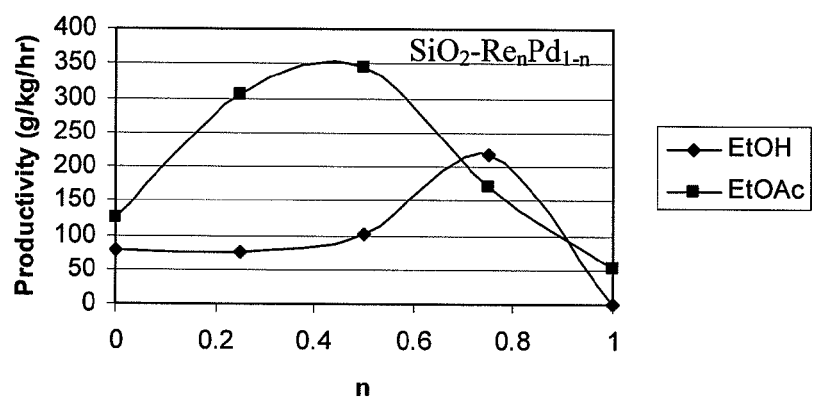
FIG. 2C - Conversion of HOAc
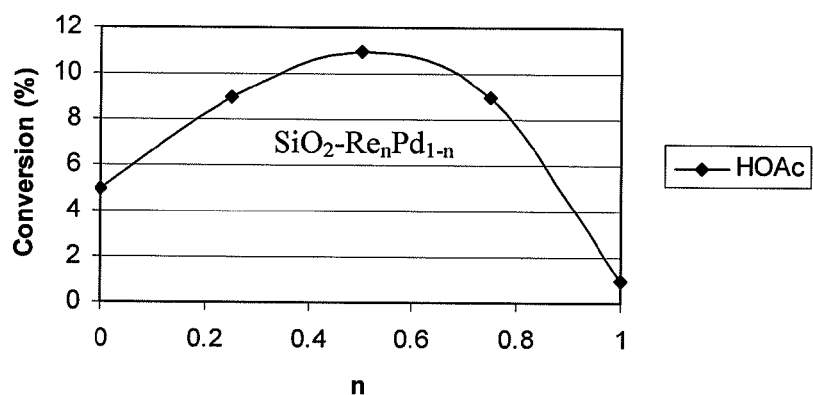

PROCESSES FOR MAKING ETHANOL FROM ACETIC ACID USING BIMETALLIC CATALYSTS

CROSS REFERENCE TO RELATED APPLICATIONS

This is a continuation-in-part of U.S. application Ser. No. 12/588,727, filed Oct. 26, 2009, entitled "Tunable Catalyst Gas Phase Hydrogenation of Carboxylic Acids," the entirety of which is incorporated herein by reference.

FIELD OF THE INVENTION

The present invention relates generally to processes for hydrogenating acetic acid to form ethanol and/or ethyl acetate depending on the molar ratio of the metals in the bimetallic catalyst.

BACKGROUND OF THE INVENTION

There is a long felt need for an economically viable process to convert acetic acid to ethanol and/or ethyl acetate. Catalytic processes for reducing alkanoic acids and other carbonyl group containing compounds have been widely studied, and a variety of combinations of catalysts, supports and operating conditions have been mentioned in the literature. The reduction of various carboxylic acids over metal oxides is reviewed by T. Yokoyama et al. in "Fine chemicals through heterogeneous catalysis. Carboxylic acids and derivatives." Chapter 8.3.1, summarizes some of the developmental efforts for hydrogenation catalysts for various carboxylic acids. (Yokoyama, T.; Setoyama, T. "Carboxylic acids and derivatives." in: "Fine chemicals through heterogeneous catalysis." 2001, 370-379.)

A series of studies by M. A. Vannice et al. concern the conversion of acetic acid over a variety of heterogeneous catalysts (Rachmady W.; Vannice, M. A.; *J. Catal.* (2002) Vol. 207, pg. 317-330.) The vapor-phase reduction of acetic acid by $H_2$ over both supported and unsupported iron was reported in a separate study. (Rachmady, W.; Vannice, M. A. *J. Catal.* (2002) Vol. 208, pg. 158-169.) Further information on catalyst surface species and organic intermediates is set forth in Rachmady, W.; Vannice, M. A., *J. Catal.* (2002) Vol. 208, pg. 170-179). Vapor-phase acetic acid hydrogenation was studied further over a family of supported Pt—Fe catalysts in Rachmady, W.; Vannice, M. A. *J. Catal.* (2002) Vol. 209, pg. 87-98) and Rachmady, W.; Vannice, M. A. *J. Catal.* (2000) Vol. 192, pg. 322-334).

Catalytic activity in for the acetic acid hydrogenation has also been reported for heterogeneous systems with rhenium and ruthenium. (Ryashentseva, M A.; Minachev, K M; Buiychev, B. M; Ishchenko, V. M.*Bull. Acad. Sci. USSR*1988, 2436-2439).

U.S. Pat. No. 5,149,680 to Kitson et al. describes a process for the catalytic hydrogenation of carboxylic acids and their anhydrides to alcohols and/or esters utilizing Group VIII metal alloy catalysts. U.S. Pat. No. 4,777,303 to Kitson et al. describes a process for the productions of alcohols by the hydrogenation of carboxylic acids. U.S. Pat. No. 4,804,791 to Kitson et al. describes another process for the production of alcohols by the hydrogenation of carboxylic acids. See also U.S. Pat. No. 5,061,671; U.S. Pat. No. 4,990,655; U.S. Pat. No. 4,985,572; and U.S. Pat. No. 4,826,795.

Malinowski et al. (*Bull. Soc. Chim. Belg.* (1985), 94(2), 93-5), discuss reaction catalysis of acetic acid on low-valent titanium heterogenized on support materials such as silica ($SiO_2$) or titania ($TiO_2$).

Bimetallic ruthenium-tin/silica catalysts have been prepared by reaction of tetrabutyl tin with ruthenium dioxide supported on silica. (Loessard et al., *Studies in Surface Science and Catalysis* (1989), Volume Date 1988, 48 (*Struct. React. Surf*), 591-600.)

The catalytic reduction of acetic acid has also been studied in, for instance, Hindermann et al., (Hindermann et al., *J. Chem. Res., Synopses* (1980), (11), 373), disclosing catalytic reduction of acetic acid on iron and on alkali-promoted iron.

Depending, for example, on market conditions, it may be desirable to control the relative amounts of ethanol and ethyl acetate that are formed in the catalytic hydrogenation of acetic acid. Thus, the need exists for processes and catalysts useful in controlling the type and relative amounts of the various products that are formed in the hydrogenation of acetic acid.

SUMMARY OF THE INVENTION

The present invention relates to processes for selectively making ethanol, ethyl acetate, or mixtures of ethanol and ethyl acetate, from the hydrogenation of acetic acid. It has now been discovered that the relative amounts of ethanol and ethyl acetate formed in the hydrogenation of acetic acid may be advantageously controlled based on the molar ratio of metals used in the hydrogenation catalyst.

In one embodiment, the catalyst comprises platinum and tin and is selective for making ethanol. In this aspect, the invention is to a process for producing ethanol, comprising hydrogenating acetic acid in the presence of a catalyst comprising a platinum, tin and at least one support, wherein the molar ratio of platinum to tin is from 0.4:0.6 to 0.6:0.4.

In another embodiment, the catalyst comprises rhenium and palladium and is selective for making ethanol. In this aspect, the invention is to a process comprising hydrogenating acetic acid in the presence of a catalyst comprising a rhenium, palladium and at least one support, wherein the molar ratio of rhenium to palladium is from 0.7:0.3 to 0.85:0.15.

In the embodiments where ethanol is the desired product, the catalyst preferably further comprises at least one support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. For example, the at least one support modifier optionally is selected from the group consisting of oxides and metasilicates of sodium, potassium, magnesium, calcium, scandium, yttrium, and zinc, and may be present in an amount of 0.1 wt. % to 50 wt. %, based on the total weight of the catalyst. The hydrogenation preferably is performed in a vapor phase at a temperature of from 125° C. to 350° C., a pressure of 10 KPa to 3000 KPa, and a hydrogen to acetic acid mole ratio of greater than 4:1.

In another embodiment, the catalyst comprises platinum and tin and is selective for making ethyl acetate. In this aspect, the invention is to a process for producing acetate, comprising hydrogenating acetic acid in the presence of a catalyst comprising a platinum, tin and at least one support, wherein the molar ratio of platinum to tin is less than 0.4:0.6 or greater than 0.6:0.4.

In another embodiment, the catalyst comprises rhenium and palladium and is selective for making ethyl acetate. In this aspect, the invention is to a process for producing acetate, comprising hydrogenating acetic acid in the presence of a catalyst comprising a rhenium, palladium and at least one support, wherein the molar ratio of rhenium to palladium is less than 0.7:0.3 or greater than 0.85:0.15.

In the embodiments where ethyl acetate is the desired product, the catalyst optionally further comprises at least one support modifier selected from the group consisting of oxides of Group IVB metals, oxides of Group VB metals, oxides of Group VIB metals, iron oxides, aluminum oxides, and mixtures thereof, e.g., at least one support modifier is selected from the group consisting of $WO_3$, $MoO_3$, $Fe_2O_3$, $Cr_2O_3$, $TiO_2$, $ZrO_2$, $Nb_2O_5$, $Ta_2O_5$, and $Al_2O_3$. The at least one support modifier, for example, may be present in an amount of 0.1 wt. % to 50 wt. %, based on the total weight of the catalyst.

In each of the above embodiments, the hydrogenation preferably is performed in a vapor phase at a temperature of from 125° C. to 350° C., a pressure of 10 KPa to 3000 KPa, and a hydrogen to acetic acid mole ratio of greater than 4:1. the support optionally is present in an amount of 25 wt. % to 99 wt. %, based on the total weight of the catalyst, and preferably has a surface area of from 50 $m^2$/g to 600 $m^2$/g. The support, for example, may be selected from the group consisting of silica, silica/alumina, calcium metasilicate, pyrogenic silica, high purity silica and mixtures thereof. The support optionally contains less than 1 wt % of aluminum, based on the total weight of the catalyst. The catalysts also preferably have a productivity that decreases less than 6% per 100 hours of catalyst usage.

According to the above embodiments, at least 10% of the acetic acid preferably is converted during hydrogenation, and preferably the hydrogenation has a selectivity to ethanol or ethyl acetate, as desired, of at least 50%, or at least 60%, and a selectivity to methane, ethane, and carbon dioxide and mixtures thereof of less than 4%.

BRIEF DESCRIPTION OF DRAWINGS

The invention is described in detail below with reference to the appended drawings, wherein like numerals designate similar parts.

FIG. 1A is a graph of the selectivity to ethanol and ethyl acetate using a $SiO_2$—$Pt_mSn_{1-m}$ catalyst according to one embodiment of the invention;

FIG. 1B is a graph of the productivity to ethanol and ethyl acetate of the catalyst of FIG. 1A;

FIG. 1C is a graph of the convention of the acetic acid of the catalyst of FIG. 1A;

FIG. 2A is a graph of the selectivity to ethanol and ethyl acetate using a $SiO_2$—$Re_nPd_{1-n}$ catalyst according to one embodiment of the invention;

FIG. 2B is a graph of the productivity to ethanol and ethyl acetate of the catalyst of FIG. 2A; and FIG. 2C is a graph of the convention of the acetic acid of the catalyst of FIG. 2A.

DETAILED DESCRIPTION OF THE INVENTION

The present invention relates to processes for producing ethanol and/or ethyl acetate by hydrogenating acetic acid in the presence of a bimetallic catalyst. It has now been discovered that the relative amounts of ethanol and ethyl acetate formed in the hydrogenation of acetic acid may be advantageously controlled based on the molar ratio of metals used in the hydrogenation catalyst. In one embodiment, the bimetallic catalyst comprises platinum and tin. In another embodiment, the bimetallic catalyst comprises rhenium and palladium.

The hydrogenation of acetic acid to form ethanol may be represented as follows:

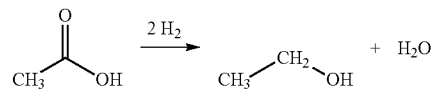

In order to favor selectivity to ethanol according to the above reaction, in embodiments where the catalyst comprises platinum and tin, the Pt/Sn molar ratio preferably is from 0.4:0.6 to 0.6:0.4, e.g., from 0.45:0.55 to 0.55:0.45 or about 1:1. In order to favor selectivity to ethanol in embodiments where the catalyst comprises rhenium and palladium, the Re/Pd molar ratio preferably is from 0.6:0.4 to 0.85:0.15, e.g., from 0.7:0.3 to 0.85:0.15, or a molar ratio of about 0.75:0.25.

The hydrogenation of acetic acid to form ethyl acetate may be represented as follows:

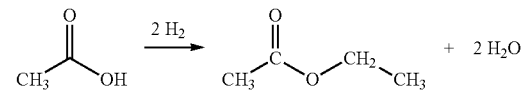

In order to favor selectivity to ethyl acetate according to the above reaction, in embodiments where the catalyst comprises platinum and tin, the Pt/Sn molar ratio preferably is less than 0.4:0.6 or greater than 0.6:0.4. More preferably, for this embodiment, the Pt/Sn molar ratio is from 0.65:0.35 to 0.95:0.05, e.g., from 0.7:0.3 to 0.95:0.05. In another embodiment, the Pt/Sn molar ratio is from 0.05:0.95 to 0.35:0.65. In order to favor selectivity to ethyl acetate in embodiments where the catalyst comprises rhenium and palladium, the Re/Pd molar ratio preferably is less than 0.7:0.3 or greater than 0.85:0.15. More preferably, for this embodiment, the Pt/Sn molar ratio is from 0.05:0.95 to 0.7:0.3, e.g., from 0.1:0.9 to 0.6:0.4. In another embodiment, the Pt/Sn molar ratio is from 0.85:0.15 to 0.95:0.05.

It should be understood that in processes that use catalysts favoring ethanol formation, ethyl acetate may also be formed, and conversely, for processes that use catalysts favoring ethyl acetate formation, ethanol may also be formed. For purposes of the present invention, a catalyst favors ethanol or ethyl acetate formation when the selectivity to one product is greater than the other. According to embodiments of the present invention, selectivities to ethanol or ethyl acetate that are greater than 50%, e.g., greater than 75% or greater than 80%, may be achieved.

For purposes of the present invention, the term conversion refers to the amount of acetic acid in the feed that is convert to a compound other than acetic acid. Conversion is expressed as a mole percentage based on acetic acid in the feed. The conversion of acetic acid (AcOH) is calculated from gas chromatography (GC) data using the following equation:

$$AcOH\ Conv.(\%) = 100 * \frac{\text{mmol AcOH (feed stream)} - \text{mmol AcOH } (GC)}{\text{mmol AcOH (feed stream)}}$$

For purposes of the present invention, the conversion may be at least 10%, e.g., at least 20%, at least 40%, at least 50%, at least 60%, at least 70% or at least 80%. Although catalysts that have high conversions are desirable, such as at least 80% or at least 90%, a low conversion may be acceptable at high selectivity to the desired product, e.g., either ethanol or ethyl acetate. It is, of course, well understood that in many cases it is possible to compensate for poor conversion by incorporating recycle streams or using larger reactors, while it is typically more difficult to compensate for poor selectivity.

"Selectivity," as used herein, is expressed as a mole percent based on converted acetic acid. It should be understood that each compound converted from acetic acid has an independent selectivity and that selectivity is independent of conversion. For example, if 50 mole % of the converted acetic acid is converted to ethanol, we refer to the ethanol selectivity as 50%.

Selectivity to ethanol (EtOH) is calculated from gas chromatography (GC) data using the following equation:

$$EtOH\ Sel.(\%) = 100 * \frac{\text{mmol } EtOH\ (GC)}{\frac{\text{Total mmol } C\ (GC)}{2} - \text{mmol AcOH (feed stream)}}$$

wherein "Total mmol C (GC)" refers to total mmols of carbon from all of the products analyzed by gas chromatograph. Of course, selectivity to ethyl acetate may be similarly calculated by substituting mmol EtOAc (GC) for mmol EtOH (GC) in the above equation.

For purposes of the present invention, the selectivity to ethoxylates of the catalyst preferably is at least 60%, e.g., at least 70%, or at least 80%. As used herein, the term "ethoxylates" refers specifically to the compounds ethanol and ethyl acetate. In embodiments where ethanol is the desired product, the selectivity to ethanol preferably is at least 60%, e.g., at least 75% or at least 80%. In embodiments where ethyl acetate is the desired product, the selectivity to ethyl acetate preferably is at least 50%, e.g., at least 75% or at least 80%. It is also generally desirable to have low selectivity to undesirable products, such as methane, ethane, and carbon dioxide. The selectivity to these undesirable products preferably is less than 4%, e.g., less than 2% or less than 1%. Ideally, no detectable amounts of these undesirable products are formed during hydrogenation. In several embodiments of the present invention, formation of alkanes is low. For example, in some embodiments, less than 2%, less 1%, or less than 0.5% of the acetic acid passed over the catalyst is converted to alkanes, which have little value other than as fuel.

In embodiments of the present invention, the first metal, e.g., platinum or palladium, optionally is present in the catalyst in an amount from 0.1 to 10 wt. %, e.g. from 0.1 to 5 wt. %, or from 0.1 to 3 wt. %. The second metal, e.g., tin or rhenium, preferably is present in an amount from 0.1 and 20 wt. %, e.g., from 0.1 to 10 wt. %, or from 0.1 to 5 wt. %. In such catalysts the two or more metals may be alloyed with one another or may comprise a non-alloyed solid solution or mixture. Unless otherwise indicated, all catalyst metal loadings expressed herein are provided in weight percent, based on the total weight of the catalyst including all metals, support and support modifier, if present.

In some embodiments, the catalyst further comprises a third metal, which preferably is selected from the group consisting of cobalt, palladium, ruthenium, copper, zinc, platinum, tin, and rhenium. More preferably, the third metal, if present, is selected from cobalt, palladium, and ruthenium. When present, the total weight of the third metal preferably is from 0.05 and 4 wt. %, e.g., from 0.1 to 3 wt. %, or from 0.1 to 2 wt. %.

Depending primarily on how the catalyst is manufactured, the metals of the catalysts of the present invention may be dispersed throughout the support, coated on the outer surface of the support (egg shell) or decorated on the surface of the support.

In addition to metals, the catalysts of the present invention further comprise a support that optionally includes a support modifier. As will be appreciated by those of ordinary skill in the art, the support material should be selected such that the catalyst system is suitably active, selective and robust under the process conditions employed for the formation of the desired product, e.g., ethanol and/or ethyl acetate. Suitable support materials may include, for example, stable metal oxide-based supports or ceramic-based supports as well as molecular sieves, such as zeolites. Examples of suitable support materials include without limitation, iron oxide, silica, alumina, silica/aluminas, titania, zirconia, magnesium oxide, a Group IIA silicate such as calcium metasilicate, carbon, graphite, high surface area graphitized carbon, activated carbons, and mixtures thereof.

Preferred supports include silica, silica/alumina, a Group IIA silicate such as calcium metasilicate, pyrogenic silica, high purity silica and mixtures thereof. It has now been discovered that increasing acidity of the support tends to increase selectivity to ethyl acetate over ethanol, and vice versa. Thus, in the case where silica is used as the support, it may be beneficial, particularly if ethanol is the desired product, to ensure that the amount of aluminum, which is a common acidic contaminant for silica, is low, preferably under 1 wt. %, e.g., under 0.5 wt. % or under 0.3 wt. %, based on the total weight of the modified support. In this regard, pyrogenic silica may be preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. The aluminum content of such silica, for example, may be less than 10 wt. %, e.g., less than 5 wt. % or less than 3 wt. %, based on the total weight of the silica including any contaminants contained therein. When calcium metasilicate is used as a support modifier, it is not necessary to be quite as strict about the purity of the silica used as the support material even if the desired product is ethanol. In cases where the support comprises a basic support modifier in the range of from 2 wt. % to 10 wt. %, larger amount of acidic impurities, such as aluminum, can be tolerated so long as they are substantially counter-balanced by an appropriate amount of a support modifier.

The surface area of the support material, optionally silicaceous support material, preferably is at least about 50 m$^2$/g, e.g., at least about 100 m$^2$/g, at least about 150 m$^2$/g, at least about 200 m$^2$/g or at least about 250 m$^2$/g. In terms of ranges, the siliceous support material preferably has a surface area of from 50 to 600 m$^2$/g, e.g., from 100 to 500 m$^2$/g or from 100 to 300 m$^2$/g. High surface area silica, as used throughout the application, refers to silica having a surface area of at least about 250 m$^2$/g. For purposes of the present specification, surface area refers to BET nitrogen surface area, meaning the surface area as determined by ASTM D6556-04, the entirety of which is incorporated herein by reference.

The support material, e.g., siliceous support material, also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 cm$^3$/g, e.g., from 0.7 to 1.5 cm$^3$/g or from about 0.8 to 1.3 cm$^3$/g, as determined by mercury intrusion porosimetry.

The morphology of the support material, and hence the morphology of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the support material, e.g., silicaceous support material, has a morphology that allows for a packing density of from 0.1 to 1.0 g/cm$^3$, e.g., from 0.2 to 0.9 g/cm$^3$ or from 0.5 to 0.8 g/cm$^3$. In terms of size, the support material preferably has an average particle size, meaning the diameter for spherical particles or equivalent spherical diameter for non-spherical particles, of from 0.01 to 1.0 cm, e.g., from 0.1 to 0.5 cm or from 0.2 to 0.4 cm. Since the metals that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint Gobain N or Pro. The Saint-Gobain N or Pro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$ (22 lb/ft$^3$).

A preferred silica/alumina support material is KA-160 (Sud Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

The total weight of the support, optionally including the support modifier, based on the total weight of the catalyst, preferably is from 75 wt. % to 99.9 wt. %, e.g., from 78 wt. % to 97 wt. %, or from 80 wt. % to 95 wt. %.

As indicated above, in some embodiments, the support further comprises a support modifier, which, for example, may adjust the acidity of the support material. The acidity of the support material may be adjusted, for example, by incorporating one or more of a basic support modifier, an acidic support modifier or a redox support modifier.

In one embodiment, the acid sites, e.g., Brønsted acid sites, on the support material may be adjusted by the support modifier to favor selectivity to ethanol or ethyl acetate, as desired, during the hydrogenation of acetic acid. The acidity of the support material may be adjusted to favor formation of ethanol, for example, by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

In preferred embodiments, particularly for the formation for ethanol, the support comprises a basic support modifier having a low volatility or that is non-volatile. Low volatility modifiers have a rate of loss that is low enough such that the acidity of the support modifier is not reversed during the life of the catalyst. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used in various embodiments of the present invention. In preferred embodiments for the formation of ethanol, the support modifier is selected from the group consisting of oxides and metasilicates of any of sodium, potassium, magnesium, calcium, scandium, yttrium, and zinc, and mixtures of any of the foregoing. In a particularly preferred embodiment, the support modifier is a calcium silicate, more preferably calcium metasilicate (CaSiO$_3$). If the support modifier comprises calcium metasilicate, it is preferred that at least a portion of the calcium metasilicate is in crystalline form. In preferred embodiments for the formation of ethanol, the support modifier comprises a basic support modifier in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

In one embodiment, which is preferred for the formation of ethanol, the catalyst includes a modified support comprising a support material and calcium metasilicate as support modifier in an amount effective to balance Brønsted acid sites resulting, for example, from residual alumina in the silica. For example, the calcium metasilicate may be present in an amount from 1 wt. % to 10 wt. %, based on the total weight of the catalyst, in order to ensure that the support is essentially neutral or basic in character.

As the support modifier, e.g., calcium metasilicate, may tend to have a lower surface area than the support material, e.g., silicaceous support material, in one embodiment the support material comprises a silicaceous support material that includes at least about 80 wt. %, e.g., at least about 85 wt. % or at least about 90 wt. %, high surface area silica in order to counteract this effect of including a support modifier.

In another embodiment, which generally is preferred for the formation of ethyl acetate, the support comprises an acidic or redox support modifier. Examples of such support modifiers include, for example, those selected from the group consisting of oxides of Group IVB metals, oxides of Group VB metals, oxides of Group VIB metals, iron oxides, aluminum oxides, and mixtures thereof. Preferred redox support modifiers include those selected from the group consisting of WO$_3$, MoO$_3$, Fe$_2$O$_3$, and Cr$_2$O$_3$. Preferred acidic support modifiers include those selected from the group consisting of TiO$_2$, ZrO$_2$, Nb$_2$O$_5$, Ta$_2$O$_5$, and Al$_2$O$_3$. In these aspects, the support modifier preferably has a low volatility or is non-volatile. Low volatility modifiers have a rate of loss that is low enough such that the acidity of the support modifier is not reversed during the life of the catalyst.

Catalysts of the present invention are particulate catalysts in the sense that, rather than being impregnated in a wash coat onto a monolithic carrier similar to automotive catalysts and diesel soot trap devices, the catalysts of the invention preferably are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. As indicated above, any convenient particle shape including pellets, extrudates, spheres, spray dried microspheres, rings, pentarings, trilobes, quadrilobes and multi-lobal shapes may be used, although cylindrical pellets are preferred. Typically, the shapes are chosen empirically based upon perceived ability to contact the vapor phase with the catalytic agents effectively.

One advantage of catalysts of the present invention is the stability or activity of the catalyst for producing ethanol and/or ethyl acetate. Accordingly, it can be appreciated that the catalysts of the present invention are fully capable of being used in commercial scale industrial applications for hydrogenation of acetic acid, particularly in the production of ethanol and/or ethyl acetate. In particular, it is possible to achieve such a degree of stability such that catalyst activity will have rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment, when the catalyst support comprises high purity silica, with calcium metasilicate as a support modifier, the catalyst activity may extend or stabilize, the productivity and selectivity of the catalyst for prolonged periods extending into over one week, over two weeks, and even months, of commercially viable operation in the presence of acetic acid vapor at temperatures of 125° C. to 350° C. at space velocities of greater than 2500 $hr^{-1}$.

The catalyst compositions of the invention preferably are formed through metal impregnation of the support or modified support, although other processes such as chemical vapor deposition may also be employed. Before the metals are impregnated, it typically is desired to form the modified support, when necessary, through a step of impregnating the support with the support modifier. A precursor to the support modifier, such as an acetate or a nitrate, may be used. In one aspect, the support modifier, e.g., $CaSiO_3$, is added to the support material, e.g., $SiO_2$. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed. Calcining of the shaped modified support may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In a preferred method of preparing the catalyst, the metals are impregnated onto the support or modified support. A precursor of the first metal (first metal precursor) preferably is used in the metal impregnation step, such as a water soluble compound or water dispersible compound/complex that includes the first metal of interest. Depending on the metal precursor employed, the use of a solvent, such as water, glacial acetic acid or organic solvent, may be preferred. The second metal also preferably is impregnated into the support or modified support from a second metal precursor. If desired, a third metal or third metal precursor may also be impregnated into the support or modified support.

Impregnation occurs by adding, optionally drop wise, either or both the first metal precursor and/or the second metal precursor and/or additional metal precursors, preferably in suspension or solution, to the dry support or modified support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the first and second metals (and optional additional metals) into the support or modified support may occur simultaneously (co-impregnation) or sequentially. In simultaneous impregnation, the first and second metal precursors (and optionally additional metal precursors) are mixed together and added to the support or modified support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the two precursors are incompatible with the desired solvent, e.g., water.

In sequential impregnation, the first metal precursor is first added to the support or modified support followed by drying and calcining, and the resulting material is then impregnated with the second metal precursor followed by an additional drying and calcining step to form the final catalyst composition. Additional metal precursors (e.g., a third metal precursor) may be added either with the first and/or second metal precursor or an a separate third impregnation step, followed by drying and calcination. Of course, combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. A particularly preferred precursor to platinum is platinum ammonium nitrate, $Pt(NH_3)_4(NO_4)_2$. Generally, both from the point of view of economics and environmental aspects, aqueous solutions are preferred. In one embodiment, the first metal precursor and the second metal precursor are not metal halides and are substantially free of metal halides. Without being bound to theory, such non-(metal halide) precursors are believed to increase selectivity to ethanol.

In one aspect, the "promoter" metal or metal precursor is first added to the support, e.g., modified support, followed by the "main" or "primary" metal or metal precursor. Of course the reverse order of addition is also possible. Exemplary precursors for promoter metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the two principal metals, e.g., Pt and Sn.

As an example, $PtSn/CaSiO_3$ on $SiO_2$ may be prepared by first impregnating $CaSiO_3$ onto the $SiO_2$, followed by co-impregnation with $Pt(NH_3)_4(NO_4)_2$ and $Sn(AcO)_2$. Again, each impregnation step may be followed by drying and calcination steps. In most cases, the impregnation may be carried out using metal nitrate solutions. However, various other soluble salts, which upon calcination release metal ions, can also be used. Examples of other suitable metal salts for impregnation include, metal acids, such as perrhenic acid solution, metal oxalates, and the like. In those cases where substantially pure ethanol is to be produced, it is generally preferable to avoid the use of halogenated precursors for the platinum group metals, using the nitrogenous amine and/or nitrate based precursors instead.

The process of hydrogenating acetic acid to form ethanol and/or ethyl acetate according to one embodiment of the invention may be conducted in a variety of configurations using a fixed bed reactor or a fluidized bed reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 10 KPa to 3000 KPa (about 0.1 to 30 atmospheres), e.g., from 50 KPa to 2300 KPa, or from 100 KPa to 1500 KPa. The reactants may be fed to the reactor at a gas hourly space velocities (GHSV) of greater than 500 $hr^{-1}$, e.g., greater than 1000 $hr^{-1}$, greater than 2500 $hr^{-1}$ and even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

In another aspect of the process of this invention, the hydrogenation is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $^-$.

The actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

Productivity refers to the grams of a specified product, e.g., ethanol or ethyl acetate, formed during the hydrogenation based on the kilogram of catalyst used per hour. For embodiments where ethanol is the preferred product, a productivity of at least 200 grams of ethanol per kilogram catalyst per hour, e.g., at least 400 grams of ethanol or least 600 grams of ethanol, is preferred. In terms of ranges, the productivity preferably is from 200 to 3,000 grams of ethanol per kilogram catalyst per hour, e.g., from 400 to 2,500 or from 600 to 2,000.

If ethyl acetate is the desired production, a productivity of at least 200 grams of ethyl acetate per kilogram catalyst per hour, e.g., at least 400 grams of ethyl acetate or least 600 grams of ethyl acetate, is preferred. In terms of ranges, the productivity preferably is from 200 to 3,000 grams of ethyl acetate per kilogram catalyst per hour, e.g., from 400 to 2,500 or from 600 to 2,000.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377 to Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. See also, U.S. Pat. No. 5,821,111 to Grady et al., which discloses a process for converting waste biomass through gasification into synthesis gas as well as U.S. Pat. No. 6,685,754 to Kindig et al., the disclosures of which are incorporated herein by reference.

Alternatively, acetic acid in vapor form may be taken directly as crude product from the flash vessel of a methanol carbonylation unit of the class described in U.S. Pat. No. 6,657,078 to Scates et al., the entirety of which is incorporated herein by reference. The crude vapor product, for example, may be fed directly to the ethanol synthesis reaction zones of the present invention without the need for condensing the acetic acid and light ends or removing water, saving overall processing costs.

Ethanol, obtained from hydrogenation processes of the present invention, may be used in its own right as a fuel or subsequently converted to ethylene which is an important commodity feedstock as it can be converted to polyethylene, vinyl acetate and/or ethyl acetate or any of a wide variety of other chemical products. For example, ethylene can also be converted to numerous polymer and monomer products. The dehydration of ethanol to ethylene is shown below.

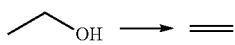

Any of known dehydration catalysts can be employed in to dehydrate ethanol, such as those described in copending applications U.S. application Ser. Nos. 12/221,137 and 12/221,138, the entire contents and disclosures of which are hereby incorporated by reference. A zeolite catalyst, for example, may be employed as the dehydration catalyst. While any zeolite having a pore diameter of at least about 0.6 nm can be used, preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

Ethanol may also be used as a fuel, in pharmaceutical products, cleansers, sanitizers, hydrogenation transport or consumption. Ethanol may also be used as a source material for making ethyl acetate, aldehydes, and higher alcohols, especially butanol. In addition, any ester, such as ethyl acetate, formed during the process of making ethanol according to the present invention may be further reacted with an acid catalyst to form additional ethanol as well as acetic acid, which may be recycled to the hydrogenation process.

Ethyl acetate obtained by the present invention, may be used in its own right, polymerized, or converted to ethylene through a cracking process. The cracking of ethyl acetate to ethylene is shown below.

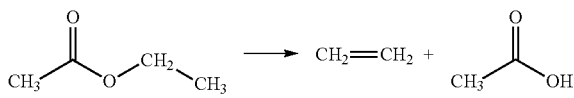

The cracking may be a catalyzed reaction utilizing a cracking catalyst. Suitable cracking catalysts include sulfonic acid resins such as perfluorosulfonic acid resins disclosed in U.S. Pat. No. 4,399,305, noted above, the disclosure of which is incorporated herein by reference. Zeolites are also suitable as cracking catalysts as noted in U.S. Pat. No. 4,620,050, the disclosure of which is also incorporated herein by reference.

The invention is described in detail below with reference to numerous embodiments for purposes of exemplification and illustration only. Modifications to particular embodiments within the spirit and scope of the present invention, set forth in the appended claims, will be readily apparent to those of skill in the art.

The following examples describe the procedures used for the preparation of various catalysts employed in the process of this invention.

EXAMPLES

Catalyst Preparations (general)

The catalyst supports were dried at 120° C. overnight under circulating air prior to use. All commercial supports (i.e., $SiO_2$, $ZrO_2$) were used as a 14/30 mesh, or in its original shape (1/16 inch or 1/8 inch pellets) unless mentioned otherwise. Powdered materials (i.e., $CaSiO_3$) were pelletized, crushed and sieved after the metals had been added. The individual catalyst preparations are described in detail below.

Examples 1-5

$SiO_2$—$Pt_mSn_{1-m}$ (0<m<1)

Five materials were prepared varying the mole fraction of Pt while maintaining a total metal amount (Pt+Sn) of 1.20 mmol. The following preparation describes the procedure for Example 1, $SiO_2$—$Pt_{0.5}Sn_{0.5}$ (i.e., m=0.5; equimolar ratio of both metals). The remaining preparations (i.e., m=0, 0.25, 0.75, and 1.00; Examples 2, 3, 4, and 5 respectively) were carried out identically using the appropriate amounts of the metal precursors $Pt(NH_3)_4(NO_3)_2$ and $Sn(OAc)_2$. The catalysts were prepared by first adding $Sn(OAc)_2$ (tin acetate, $Sn(OAc)_2$ from Aldrich) (0.1421 g, 0.60 mmol) to a vial containing 6.75 ml of 1:1 diluted glacial acetic acid (Fisher). The mixture was stirred for 15 min at room temperature, and then, 0.2323 g (0.60 mmol) of solid $Pt(NH_3)_4(NO_3)_2$ (Aldrich) were added. The mixture was stirred for another 15 min at room temperature, and then added drop wise to 5.0 g of dry $SiO_2$ catalyst support (high purity silica catalyst support HSA SS #61138, SA=250 m²/g; SZ #61152, SA=156 m²/g; Saint-Gobain N or Pro), in a 100 ml round-bottomed flask. The metal solution was stirred continuously until all of the Pt/Sn mixture had been added to the $SiO_2$ catalyst support while rotating the flask after every addition of metal solution. After completing the addition of the metal solution, the flask containing the impregnated catalyst was left standing at room temperature for two hours. The flask was then attached to a rotor evaporator (bath temperature 80° C.), and evacuated until dried while slowly rotating the flask. The material was then dried further overnight at 120° C., and then calcined using the following temperature program: 25→160° C./ramp 5.0 deg/min; hold for 2.0 hours; 160→500° C./ramp 2.0 deg/min; hold for 4 hours. Yield: 5.2 g of dark grey material.

In Example 1 the weight percentage of the catalyst is 2.3 wt. % platinum and 1.4 wt. % tin. The weight percent in Example 3 is 1.1 wt. % platinum and 2.1 wt. % tin and Example 4 is 3.4 wt. % platinum and 0.7 wt. % tin. Example 2, which contains no platinum, contains 2.7 wt % of tin and Example 5, which contains no tin, contains 4.5 wt % of platinum.

15

Example 6

SiO$_2$—CaSiO$_3$(5)-Pt(3)-Sn(1.8)

The material was prepared by first adding CaSiO$_3$ (Aldrich) to the SiO$_2$ catalyst support, followed by the addition of Pt/Sn as described previously. First, an aqueous suspension of CaSiO$_3$(≤200 mesh) was prepared by adding 0.52 g of the solid to 13 ml of deionized H$_2$O, followed by the addition of 1.0 ml of colloidal SiO$_2$ (15 wt % solution, NALCO). The suspension was stirred for 2 hours at room temperature and then added to 10.0 g of SiO$_2$ catalyst support (14/30 mesh) using incipient wetness technique. After standing for 2 hours, the material was evaporated to dryness, followed by drying at 120° C. overnight under circulating air and calcination at 500° C. for 6 hours. All of the SiO$_2$—CaSiO$_3$ material was then used for Pt/Sn metal impregnation using 0.6711 g (1.73 mmol) of Pt(NH$_3$)$_4$(NO$_3$)$_2$ and 0.4104 g (1.73 mmol) of Sn(OAc)$_2$ following the procedure described above for the Examples 1-5. Yield: 11.21 g of dark grey material.

Examples 7-11

SiO$_2$—Re$_n$Pd$_{1-n}$(0<n<1)

Five materials were prepared varying the mol fraction of Re while maintaining a total metal amount (Re+Pd) of 1.20 mmol. The following preparation describes the procedure for SiO$_2$—Re$_{0.5}$Pd$_{0.5}$ (i.e., n=0.5; equimolar ratio of both metals). The remaining preparations (i.e., x=0, 0.25, 0.75, and 1.00) were carried out identically using the appropriate amounts of the metal precursors NH$_4$ReO$_4$ and Pd(NO$_3$)$_2$. The metal solutions were prepared by first adding NH$_4$ReO$_4$ (0.1609 g, 0.60 mmol) to a vial containing 6.75 ml of deionized H$_2$O. The mixture was stirred for 15 min at room temperature, and 0.1154 g (0.60 mmol) of solid Pd(NO$_3$)$_2$ was then added. The mixture was stirred for another 15 min at room temperature, and then added drop wise to 5.0 g of dry SiO$_2$ catalyst support (14/30 mesh) in a 100 ml round-bottomed flask. After completing the addition of the metal solution, the flask containing the impregnated catalyst was left standing at room temperature for two hours. The flask was then attached to a rotor evaporator (bath temperature 80° C.), and evacuated to dryness. All other manipulations (drying, calcination) were carried out as described above for Examples 1-5. Yield: 5.1 g of a brown material.

Example 12

Hydrogenation of Acetic Acid over Catalysts from Examples 1-11 and Gas Chromatographic (GC) Analysis of the Crude Ethanol Product Catalyst of Examples 1-11 were tested to determine the selectivity and productivity to ethanol as shown in Table 1.

The reaction feed liquid of acetic acid was evaporated and charged to the reactor along with hydrogen and helium as a carrier gas with an average combined gas hourly space velocity (GHSV), temperature, and pressure as indicated in Table 1. The feed stream contained a mole ratio hydrogen to acetic acid as indicated in Table 1. FIGS. 1A-1C also illustrate the performance of the catalyst from Examples 1-5 and FIGS. 2A-2C illustrate the performance of the catalyst from Examples 7-11.

The analysis of the products (crude ethanol composition) was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify: Acetaldehyde; Ethanol; Acetone; Methyl acetate; Vinyl acetate; Ethyl acetate; Acetic acid; Ethylene glycol diacetate; Ethylene glycol; Ethylidene diacetate; and Paraldehyde. The middle channel was equipped with a TCD and Porabond Q column and was used to quantify: CO$_2$; ethylene; and ethane. The back channel was equipped with a TCD and Molsieve 5A column and was used to quantify: Helium; Hydrogen; Nitrogen; Methane; and Carbon monoxide.

Prior to reactions, the retention times of the different components were determined by spiking with individual compounds and the GCs were calibrated either with a calibration gas of known composition or with liquid solutions of known compositions. This allowed the determination of the response factors for the various components.

TABLE 1

| Cat. Ex. | Cat. | Ratio of H$_2$:AcOH | Press. (KPa) | Temp. (°C.) | GHSV (hr$^{-1}$) | Conv. of AcOH (%) | Selectivity (%) EtOAc | EtOH |
|---|---|---|---|---|---|---|---|---|
| 1 | SiO$_2$—Pt$_m$—Sn$_{1-m}$ (m = 0.5) | 5:1 | 2200 | 250 | 2500 | 73 | 26 | 74 |
| 2 | SiO$_2$—Pt$_m$—Sn$_{1-m}$ (m = 0) | 5:1 | 2200 | 250 | 2500 | — | — | — |
| 3 | SiO$_2$—Pt$_m$—Sn$_{1-m}$ (m = 0.25) | 5:1 | 2200 | 250 | 2500 | 28 | 56 | 44 |
| 4 | SiO$_2$—Pt$_m$—Sn$_{1-m}$ (m = 0.75) | 5:1 | 2200 | 250 | 2500 | 17 | 72 | 28 |
| 5 | SiO$_2$—Pt$_m$—Sn$_{1-m}$ (m = 1) | 5:1 | 2200 | 250 | 2500 | 3 | 100 | — |
| 6 | SiO$_2$—CaSiO$_3$(5)—Pt(3)—Sn(1.8) | 5:1 | 2200 | 250 | 2500 | 24 | 6 | 92 |
| 7 | SiO$_2$—Re$_n$Pd$_{1-n}$ (n = 0.5) | 5:1 | 2200 | 250 | 2500 | 11 | 77 | 23 |
| 8 | SiO$_2$—Re$_n$Pd$_{1-n}$ (n = 0) | 5:1 | 2200 | 250 | 2500 | 5 | 62 | 38 |
| 9 | SiO$_2$—Re$_n$Pd$_{1-n}$ (n = 0.25) | 5:1 | 2200 | 250 | 2500 | 9 | 80 | 20 |
| 10 | SiO$_2$—Re$_n$Pd$_{1-n}$ (n = 0.75) | 5:1 | 2200 | 250 | 2500 | 9 | 44 | 56 |
| 11 | SiO$_2$—Re$_n$Pd$_{1-n}$ (n = 1) | 5:1 | 2200 | 250 | 2500 | 1 | 100 | — |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising hydrogenating acetic acid in the presence of a catalyst comprising platinum, tin and at least one support, wherein the molar ratio of platinum to tin is from 0.4:0.6 to 0.6:0.4.

2. The process of claim 1, wherein the support is present in an amount of 25 wt. % to 99 wt. %, based on the total weight of the catalyst.

3. The process of claim 1, wherein the support has a surface area of from 50 m$^2$/g to 600 m$^2$/g.

4. The process of claim 1, wherein the support is selected from the group consisting of silica, silica/alumina, calcium metasilicate, pyrogenic silica, high purity silica and mixtures thereof.

5. The process of claim 4, wherein the support contains less than 1 wt % of aluminum, based on the total weight of the catalyst.

6. The process of claim 1, wherein the catalyst further comprises at least one support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

7. The process of claim 6, wherein the at least one support modifier is selected from the group consisting of oxides and metasilicates of sodium, potassium, magnesium, calcium, scandium, yttrium, and zinc.

8. The process of claim 6, wherein the at least one support modifier is present in an amount of 0.1 wt. % to 50 wt. %, based on the total weight of the catalyst.

9. The process of claim 1, wherein at least 10% of the acetic acid is converted during hydrogenation.

10. The process of claim 1, wherein the hydrogenation has a selectivity to ethanol of at least 60%.

11. The process of claim 10, wherein the hydrogenation has a selectivity to methane, ethane, and carbon dioxide and mixtures thereof of less than 4%.

12. The process of claim 1, wherein the catalyst has a productivity that decreases less than 6% per 100 hours of catalyst usage.

13. The process of claim 1, wherein the acetic acid is obtained from a coal source, natural gas source or biomass source.

14. The process of claim 1, wherein the hydrogenation is performed in a vapor phase at a temperature of from 125° C. to 350° C., a pressure of 10 KPa to 3000 KPa, and a hydrogen to acetic acid mole ratio of greater than 4:1.

* * * * *